US006958078B2

(12) United States Patent
Goel et al.

(10) Patent No.: US 6,958,078 B2
(45) Date of Patent: Oct. 25, 2005

(54) BIOARTIFICIAL INTERVERTEBRAL DISC

(75) Inventors: Vijay K. Goel, Toledo, OH (US); Ronald L. Fournier, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 10/223,275

(22) Filed: Aug. 19, 2002

(65) Prior Publication Data

US 2004/0034427 A1   Feb. 19, 2004

(51) Int. Cl.[7] .............................. A61F 2/44; A61F 2/54
(52) U.S. Cl. .................. 623/17.16; 623/66.1
(58) Field of Search ................... 623/17.11, 17.16, 623/23.51, 23.57, 23.58, 23.61, 23.63, 23.74, 623/23.75, 23.76

(56) References Cited

U.S. PATENT DOCUMENTS

| | | | | |
|---|---|---|---|---|
| 5,047,055 | A | * | 9/1991 | Bao et al. ...................... 623/17 |
| 5,108,438 | A | * | 4/1992 | Stone ........................... 623/11 |
| 5,916,557 | A | | 6/1999 | Berlowitz-Tarrant et al. ........................ 424/94.5 |
| 5,964,807 | A | | 10/1999 | Gan et al. ..................... 623/17 |
| 6,113,638 | A | * | 9/2000 | Williams et al. ............... 623/17 |
| 6,197,586 | B1 | | 3/2001 | Bhatnagar et al. .......... 435/395 |
| 6,224,630 | B1 | * | 5/2001 | Bao et al. ...................... 623/17 |
| 6,240,926 | B1 | | 6/2001 | Chin Gan et al. ........... 128/898 |
| 6,306,169 | B1 | * | 10/2001 | Lee et al. ................. 623/11.11 |
| 6,340,369 | B1 | * | 1/2002 | Ferree ..................... 623/16.11 |
| 6,352,558 | B1 | | 3/2002 | Spector .................... 623/18.11 |
| 6,428,802 | B1 | | 8/2002 | Atala .......................... 424/423 |
| 6,451,060 | B2 | | 9/2002 | Masuda et al. .......... 623/23.72 |
| 6,489,165 | B2 | | 12/2002 | Bhatnagar et al. .......... 435/395 |
| 6,528,052 | B1 | * | 3/2003 | Smith et al. ............... 424/93.7 |
| 2002/0119177 | A1 | * | 8/2002 | Bowman et al. ............ 424/423 |
| 2003/0003127 | A1 | * | 1/2003 | Brown et al. ............... 424/423 |

OTHER PUBLICATIONS

Ma and Choi, "Biodegradable Polymer Scaffolds . . . ", Tissue Engineering, vol. 7, No. 1, 2001.

* cited by examiner

*Primary Examiner*—Kevin Shaver
*Assistant Examiner*—Anu Ramana
(74) *Attorney, Agent, or Firm*—MacMillan, Sobanski & Todd, LLC

(57) ABSTRACT

A bioartificial nucleus pulposus is adapted for replacing at least a portion of a natural nucleus pulposus in an intervertebral disc. The bioartificial nucleus pulposus includes an artificial support structure made from a biodegradable material. The support structure has a plurality of pores. A carrier material is contained in the pores of the support structure. A plurality of nucleus pulposus cells are carried by the carrier material. A bioartificial intervertebral disc contains the bioartificial nucleus pulposus.

6 Claims, 2 Drawing Sheets

BIOARTIFICIAL INTERVERTEBRAL DISC

BACKGROUND OF THE INVENTION

This invention relates in general to replacement body parts for humans and animals. In particular, the invention relates to a bioartificial intervertebral disc adapted for replacing a natural intervertebral disc in a spinal column of a human or animal.

Chronic low back pain is the primary cause of disability in active age groups of the society, playing a major role in the medical, social, and economic structure of industrial countries. The management of chronic low back pain is a prevalent problem to the clinician. It has been estimated that 70% of the population in the United States have experienced low back pain during their lives. While rest, medications, and therapy are the primary and preferred treatment methods, 4% of the population have still undergone surgical intervention. As the population ages, the problem will certainly grow.

Intervertebral disc degeneration and associated spinal disorders are a leading source of morbidity, resulting in substantial pain and increased health care costs. Disability of patients with low back pain creates extensive cost to the individual and society because of lost productivity and treatment costs, affecting millions of individuals. In the United States, the estimated health care cost for the treatment of chronic low back pain is 33 billion dollars per year with a total cost to society of greater than 100 billion dollars per year.

The intervertebral disc degenerates much earlier in life than other tissues. Disc degeneration begins in individuals in their twenties and increases throughout their adult life. While this does not always result in back pain, in many individuals there is significant back pain associated with disc degeneration. Disc degeneration can begin in the nucleus pulposus (NP) with a progressive decrease in proteoglycan content leading to dehydration of the NP. The swelling pressure resulting from high concentrations of proteoglycans in the NP helps to maintain disc height and contributes to the load-bearing ability of the disc. A loss of proteoglycans may directly affect the biomechanical function of intervertebral discs. It has been suggested that because the disc is the largest avascular tissue in the body, one reason for degeneration is a fall in transport of nutrients into the disc.

The current surgical treatment methods for intervertebral disc degeneration primarily involve the fusion of two vertebrae. Surgical stabilization and fusion of the spine have become increasingly common practice. Spinal fusion procedures are most commonly indicated when joint pain is a major symptom. Elimination of the relative motion between affected joints often reduces segmental pain. While there is a reduction or elimination of pain, surgical fusion leaves the patient with limited mobility.

One of the most recent developments for nonfusion surgical treatment is the total replacement of the intervertebral disc with a mechanical disc. Mechanical disc replacement designs have been classified into four categories: (1) low-friction sliding surface designs; (2) spring and hinge systems; (3) contained fluid-filled chambers; and (4) discs of rubber and other elastomers. The mechanical discs lack certain biological and mechanical properties of natural intervertebral discs.

SUMMARY OF THE INVENTION

This invention relates to a bioartificial nucleus pulposus adapted for replacing at least a portion of a natural nucleus pulposus in an intervertebral disc. The bioartificial nucleus pulposus includes an artificial support structure made from a biodegradable material. The support structure has a plurality of pores. A carrier material is contained in the pores of the support structure. A plurality of nucleus pulposus cells are carried by the carrier material.

The invention also relates to a bioartificial intervertebral disc adapted for replacing a natural intervertebral disc. The bioartificial intervertebral disc includes a hollow disc adapted for use as part of an intervertebral disc, the hollow disc comprising an annulus and first and second endplates attached to opposing faces of the annulus. A bioartificial nucleus pulposus is contained within the hollow disc. The nucleus pulposus includes a disc-shaped artificial support structure made from a biodegradable material. The support structure has a plurality of pores. A carrier material is contained in the pores of the support structure. A plurality of nucleus pulposus cells are carried by the carrier material.

The invention also relates to a method of producing a bioartificial nucleus pulposus adapted for replacing at least a portion of a natural nucleus pulposus in an intervertebral disc. The method includes forming an artificial support structure from a biodegradable material, the support structure having a plurality of pores. A plurality of nucleus pulposus cells are suspended within a carrier material. The carrier material and cells are introduced into the pores of the support structure to produce the bioartificial nucleus pulposus.

The invention further relates to a method of replacing at least a portion of a natural nucleus pulposus with a bioartificial nucleus pulposus in an intervertebral disc. The method includes forming an artificial support structure from a biodegradable material, the support structure having a plurality of pores. A plurality of nucleus pulposus cells are suspended within a carrier material. The carrier material and cells are introduced into the pores of the support structure to produce the bioartificial nucleus pulposus. At least a portion of the natural nucleus pulposus is removed from the intervertebral disc, and the bioartificial nucleus pulposus is introduced into the intervertebral disc in place of the removed natural nucleus pulposus.

The invention also relates to a method of replacing a natural intervertebral disc with a bioartificial intervertebral disc. The method includes providing a hollow disc adapted for use as part of an intervertebral disc, the hollow disc comprising an annulus and first and second endplates attached to opposing faces of the annulus. A disc-shaped artificial support structure is formed from a biodegradable material, the support structure having a plurality of pores. A plurality of nucleus pulposus cells are suspended within a carrier material. The carrier material and cells are introduced into the pores of the support structure to produce a bioartificial nucleus pulposus. The bioartificial nucleus pulposus is introduced into the hollow intervertebral disc to form the bioartificial intervertebral disc. The natural intervertebral disc is removed from between a pair of vertebrae, and the bioartificial intervertebral disc is introduced between the pair of vertebrae.

Various advantages of this invention will become apparent to those skilled in the art from the following detailed description of the preferred embodiments, when read in light of the accompanying drawings.

DETAILED DESCRIPTION OF THE PREFERRED EMBODIMENTS

Figure 1:
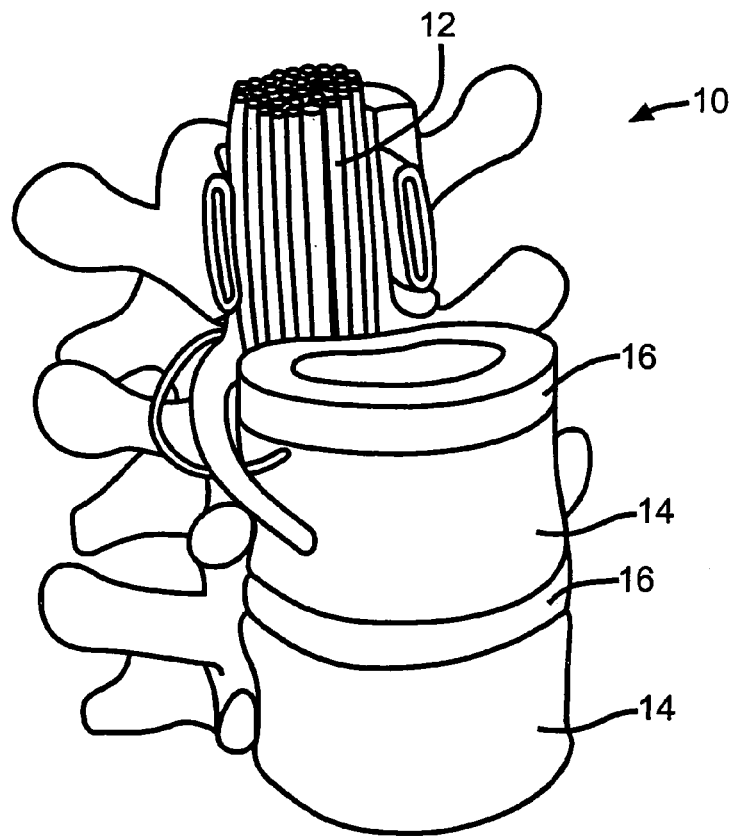
FIG. 1 is a perspective view of a lumbar portion of a human spine and spinal cord.
Figure 2:
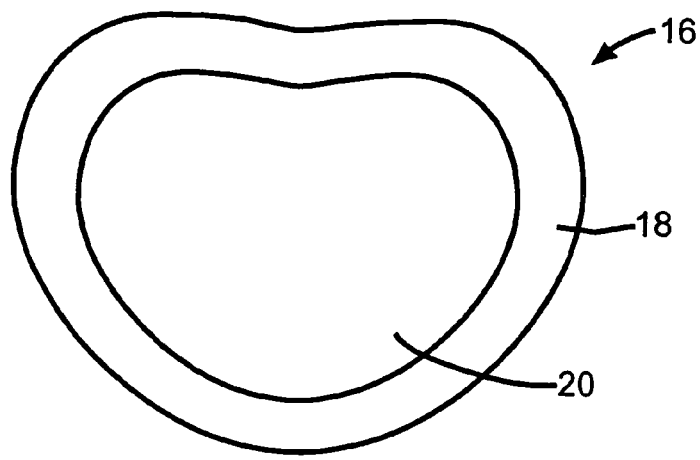
FIG. 2 is an enlarged perspective view of an intervertebral disc of the spine, showing the nucleus pulposus and the annulus fibrosus of the disc.

Referring now to the drawings, there is illustrated in FIG. 1 a lumbar portion of a human spine 10. A spinal cord 12 is enclosed in a spinal canal formed by the spine. The spine includes a plurality of bones known as vertebrae 14. The vertebrae are separated by intervertebral discs 16. FIG. 2 is an enlarged view of one of the intervertebral discs 16. The intervertebral disc is composed of an annulus fibrosus 18 encircling a nucleus pulposus 20, and thin vertebral endplates (not shown) attached to opposing faces of the annulus fibrosus to form a disc-shaped structure. The annulus fibrosus consists of concentric lamellae of collagen fibers. The endplates consist of cartilage.

The nucleus pulposus (NP) 20 located in the core of the intervertebral disc 16 plays a central role in the structural integrity and flexibility of the spine. The NP is a gel-like matrix consisting of extracellular matrix materials such as collagen and proteoglycans as well as a sparse population of nucleus pulposus cells. The presence of the polyanionic proteoglycans results in a highly hydrated state for the NP as a result of the osmotic flow of water into the NP. The presence of water in the NP, and the annulus fibrosus 18 that encircles the NP, yields a disc structure that provides significant flexibility to the spine as well as some cushioning in loading situations. Degenerative disc disease correlates with a loss of viable NP cells and a significant decrease in the amounts of proteoglycans and collagen, resulting in a loss in the degree of hydration within the NP of the disc.

As discussed above, degenerative disc disease is a leading source of chronic low back pain. The back pain can be surgically treated by fusing two vertebrae, but surgical fusion reduces the flexibility of the spine. The intervertebral disc can be removed and replaced by a mechanical disc, but mechanical discs lack certain biological and mechanical properties of natural discs. The present invention provides a bioartificial nucleus pulposus, and a bioartificial intervertebral disc including the nucleus pulposus, as alternative treatment methods for degenerative intervertebral disc disease. It is believed that the bioartificial intervertebral disc will allow the patient to maintain full flexibility and use of the spine while reducing pain. The bioartificial intervertebral disc will also possess biological and mechanical properties similar to a natural intervertebral disc.

Two options are available for treatment of degenerative disc disease using this invention. First, just the nucleus pulposus, or a degenerated portion of the nucleus pulposus, can be replaced with the bioartificial nucleus pulposus of the invention. This involves the surgical removal of the failed nucleus pulposus, or a degenerated portion thereof, followed by insertion of the bioartificial nucleus pulposus into the core of the hollowed out disc. A small section of the annulus fibrosus will be removed from the disc to allow removal of the failed nucleus pulposus and insertion of the bioartificial nucleus pulposus. Second, the entire degenerated disc can be removed and the combined bioartificial nucleus pulposus and annulus fibrosus can be inserted between the opposing faces of the vertebrae.

The bioartificial nucleus pulposus of the invention includes an artificial support structure or scaffold. If the bioartificial nucleus pulposus is intended as a total replacement for a natural nucleus pulposus, the support structure is generally disc-shaped. The support structure has a plurality of pores. Preferably, the pores have an average diameter within a range of from about 100 microns to about 1000 microns, and more preferably from about 300 microns to about 600 microns. The pore size, porosity, and surface area (surface-to-volume ratio) of the support structure affect its properties. Typically, the support structure is an open pore sponge-like structure. The support structure is made from a biodegradable material. The biodegradable material degrades as a new nucleus pulposus is formed in the spine, eventually leaving nothing foreign to the body. Any of a wide variety of biodegradable materials can be used, such as a biodegradable polymer or a combination of biodegradable polymers. Preferably, the biodegradable material is a biodegradable polymer such as poly(lactide-co-glycolide) (PLGA) or poly(lactide) (PLLA). The bioartificial nucleus pulposus should have physical properties and strength similar to the natural nucleus pulposus that it replaces. In some embodiments, the support structure has a strength of at least about 80 kPa, and more preferably at least about 100 kPa. The strength can be measured by any suitable means, such as by using a mechanical testing system (MTS). A relatively strong support structure will be able to bear some of the load from the spine while the nucleus pulposus cells grow.

Any suitable method can be used for forming the bioartificial nucleus pulposus including the support structure, such as any of a variety of different tissue engineering techniques, salt leaching, or other methods. In one method, the support structure is formed by casting a biodegradable polymer in a mold containing a plurality of dissolvable objects such as spheres. When the spheres are dissolved, the polymer is left with a plurality of pores. In a specific embodiment, the support structure is made generally according to the procedure outlined by Ma and Choi in the article "Biodegradable Polymer Scaffolds with Well-Defined Interconnected Spherical Pore Network," Tissue Engineering, 7(1): 23–33 (2001).

Figure 3:
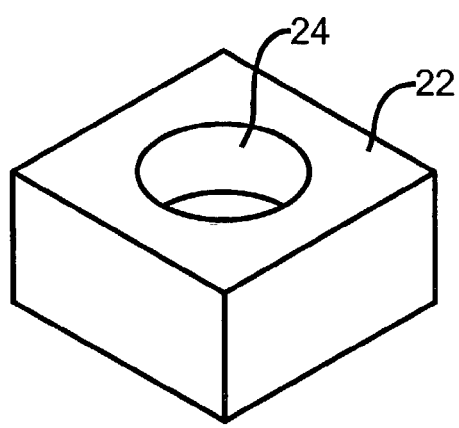
FIG. 3 is a perspective view of a mold used for forming a support structure of a bioartificial nucleus pulposus according to the invention.

FIGS. 3–6 illustrate some of the steps of this procedure. As shown in FIG. 3, a mold 22 is provided having a disc-shaped opening 24. The exact size and shape will depend on the intended use of the bioartificial nucleus pulposus; for example, a bioartificial nucleus pulposus intended for use in a human will have a different size and shape from one intended for use in an animal. The mold should have dimensions suitable for making a desired sized device for a given patient. The mold shown in FIG. 3 is relatively small and it has a relatively small opening to produce a bioartificial nucleus pulposus intended for use in a rabbit for testing of the invention. The mold can be made from any suitable material, and preferably a material that is hard and heat-resistant, and that allows for easy removal of the molded polymer. In the illustrated embodiment, the mold 22 is made from Teflon™ and the opening 24 is about 13 mm in diameter and about 5 mm deep.

Figure 4:
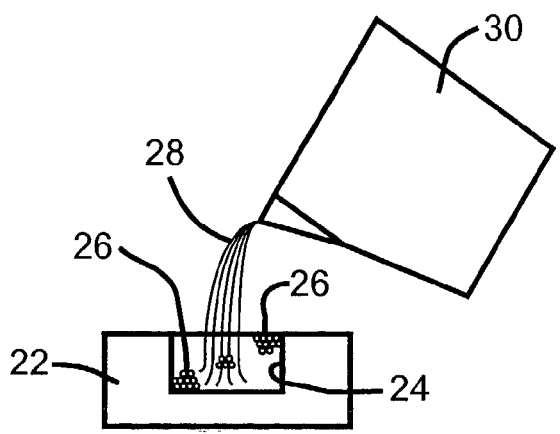
FIG. 4 is an elevational view, partly in cross-section, showing the mold containing a plurality of paraffin spheres, and showing a solution of a biodegradable polymer being cast into the mold to form the support structure.

A plurality of objects made from a dissolvable material are placed into the opening of the mold. The objects are preferably spherical in shape, but they can also be any other suitable shape. FIG. 4 shows a plurality of spheres 26 placed into the opening 24 of the mold 22. The shape, size and number of pores in the support structure will depend on the shape, size and number of objects placed into the mold. In a preferred embodiment, the spheres 26 have a diameter of about 425 microns. (The spheres 26 are shown larger in the figure for illustration purposes.) Preferably, the objects are placed adjacent to each other in the mold so that the resulting support structure has an interconnected pore network. The objects can be made from any suitable dissolvable material. In the illustrated embodiment, the spheres 26 are made from paraffin, although other materials such as various polymers could be used for making the spheres provided there is a suitable solvent for them. Preferably, after the paraffin spheres are placed into the mold, the mold is heated at a temperature and for a time sufficient to promote adhesion of the paraffin spheres to each other, e.g., a temperature of 37° C. for 20 minutes in a drying oven.

The biodegradable polymer is then introduced into the opening 24 of the mold 22. To facilitate the casting process, the biodegradable polymer is preferably dissolved in a solvent. The solvent should dissolve the polymer without dissolving the paraffin spheres. Some examples of suitable solvents include pyridine and chloroform. FIG. 4 shows a solution 28 containing a biodegradable polymer being poured from a container 30 into the mold 22. The concentration of the biodegradable polymer in the solution will affect the strength of the cast support structure. In a preferred embodiment, the solution contains poly(lactide-co-glycolide) (PLGA) dissolved in pyridine, with the PLGA or PLLA at a concentration of from about 10% to about 20% by weight of the solution, more preferably from about 12% to about 18%. After the solution is poured into the mold, the solvent is evaporated from the mold, leaving the polymer inside the mold surrounding the paraffin spheres. Preferably, the evaporation of the solvent is facilitated by use of a vacuum; the complete evaporation of pyridine can be accomplished under high vacuum in approximately five to seven days.

The strength of the cast support structure can also be increased by introducing a second solution of the biodegradable polymer into the mold over the previously cast polymer. When the solvent of the second solution is evaporated, the polymer of the second solution will be added to the polymer of the first solution (i.e., the second polymer is layered over the first polymer) to increase the thickness of the walls of the support structure surrounding the pores. This process can be repeated until the resulting support structure has the desired strength. Usually, two or three castings are performed until the support structure reaches the desired strength as determined by mechanical testing.

After the evaporation of the solvent following the last casting, the support structure is removed from the mold and placed in another solvent to dissolve the paraffin spheres. Any of a variety of different solvents that will dissolve the spheres can be used, such as hexane or cyclohexane. In a preferred method, the support structure is placed in hexane at room temperature for two days, changed twice per day, to clear the paraffin. Following hexane, the support structure is placed in cyclohexane or a similar solvent and frozen for twelve to twenty-four hours. The support structure is then removed from the cyclohexane and freeze-dried for a minimum of 2 days to completely remove the solvent. Sterilization of the support structure is accomplished by soaking in 70% ethanol for 4–7 days, followed by complete rinsing with sterile ultrapure water.

Figure 5:
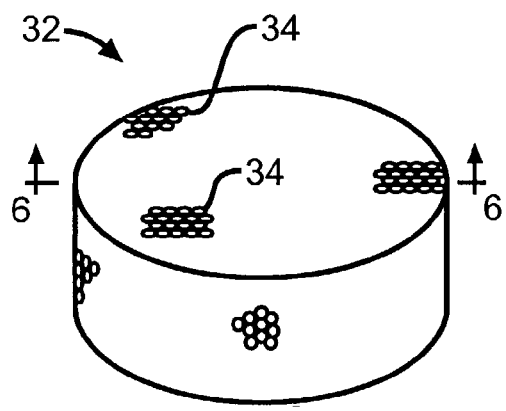
FIG. 5 is a perspective view of the resulting support structure removed from the mold.
Figure 6:
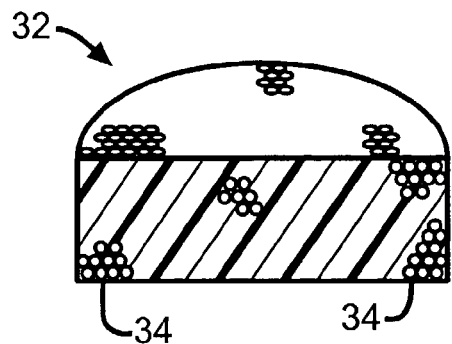
FIG. 6 is a cross-sectional view of the support structure showing a network of interconnected pores throughout the structure.

FIGS. 5 and 6 illustrate the resulting support structure 32. The support structure is a disc-shaped, sponge-like structure made from the biodegradable polymer. The support structure has a plurality of pores 34 corresponding to the previous locations of the paraffin spheres 26. Preferably, the pores form an interconnected spherical pore network throughout the support structure. FIG. 6 is a cross-sectional view of the support structure 32 showing a network of pores 34 throughout the structure.

After the support structure has been formed, a carrier material containing a plurality of donor nucleus pulposus cells is introduced into the pores of the support structure to produce the bioartificial nucleus pulposus. A natural nucleus pulposus has an extracellular matrix (ECM)-like structure, consisting of an extracellular gel-like fluid containing a variety of macromolecules. To produce a bioartificial nucleus pulposus having this structure, a carrier material is needed to stimulate the donor nucleus pulposus cells to produce the necessary components and gel-like environment of the nucleus pulposus. Any suitable carrier material can be used. Preferably, the carrier material is a hydrogel. Biological hydrogels such as Matrigel® contain the components of the ECM and are very effective in seeding the nucleus pulposus cells into the polymer support structure. Matrigel® is a solubilized basement membrane matrix that is rich in extracellular proteins, collagen, proteoglycan, growth factors, and other proteinases that serve to replicate the in vivo environment allowing the cells to retain normal function. Matrigel® is liquid at 4° C. and gels at 22°–35° C. to provide a three-dimensional matrix. A three-dimensional material promotes cell growth on the support structure walls facilitating the formation of specialized structures.

The donor nucleus pulposus cells are suspended within the carrier material, typically by gently mixing the cells into the carrier material until they are well dispersed therein. Depending on the intended use of the bioartificial nucleus pulposus, the nucleus pulposus cells can be any type of NP cells, such as donor cells from humans or animals. The concentration and number of cells in the carrier can vary depending on the type of cells and the desired properties of the bioartificial nucleus pulposus. The cells can be obtained for use in any suitable manner. For example, rabbit NP cells can be isolated by enzymatic digestion from the lumbar discs of euthanized rabbits. In one method, the cells are isolated with testicular hyaluronidase (1600 u/ml, 60 minutes) followed by collagenase (0.25 mg/ml) and Pronase E (0.1 mg/ml, 16 hours). After isolation, aliquots of the cells can be immediately frozen for long-term storage in liquid nitrogen using cell freezing media. Cells used for seeding the support structure can be cultured using standard tissue culture techniques in suitable media, such as in DMEM with 10% fetal bovine serum. The cells may be incubated for various lengths of time to determine their viability following the isolation.

Growth factor can optionally be added to the carrier material to stimulate the growth of the nucleus pulposus cells and increase synthesis of the components of the extracellular matrix. For example, transforming growth factor-β (TGF-β1), Insulin-like growth factor, IGF-1, and/or osteogenic protein-1, OP-1, can be added.

Optionally, any other desired compatible materials can also be added to the carrier material, such as specific genes for growth factors, or materials typically found in an extracellular matrix (e.g., collagen).

The carrier material containing the nucleus pulposus cells can be introduced into the pores of the support structure in any suitable manner. Typically, the carrier material is injected into the support structure such that it flows into the pores. Any suitable equipment can be used for injecting the carrier material, such as a syringe or micropipette.

The resulting bioartificial nucleus pulposus comprises the disc-shaped artificial support structure made from the biodegradable material, the carrier material contained in the pores of the support structure, and the nucleus pulposus cells and optionally growth factor carried by the carrier material. The support structure guides the growth and organization of the transplanted nucleus pulposus cells. The cells will attach to the support structure, replicate, differentiate, and organize into normal healthy nucleus pulposus tissue as the biodegradable material of the support structure degrades. The cells will establish the rich gel-like material that characterizes a natural nucleus pulposus. The resulting bioartificial nucleus pulposus is expected to have a size and shape, and structural and biomechanical properties that mimic very closely those of a natural nucleus pulposus. Following degradation of the support structure, the newly formed tissue will form a completely biological replacement of a natural nucleus pulposus.

The bioartificial nucleus pulposus will be used to replace a natural nucleus pulposus in a spine of a patient. The time at which the bioartificial nucleus pulposus is implanted into a spine can be varied. If done soon after the nucleus pulposus cells are added to the support structure, this could result in a somewhat rigid structure complicating somewhat the implantation. However, if implanted in this state the development of the bioartificial nucleus pulposus would benefit from the in vivo loading environment of the patient. On the other hand, the bioartificial nucleus pulposus can be cultured in vitro for some time before implantation, providing a bioartificial nucleus pulposus with a gel-like consistency that could be simply injected into the core of the intervertebral disc. Usually, the bioartificial nucleus pulposus is cultured in vitro for at least about 1 week, and typically about 1 to 2 weeks.

Preferably, the bioartificial nucleus pulposus is subjected to a load while it is cultured in vitro. It is believed that the nucleus pulposus cells respond to an applied load by increasing their cell division rate and their synthesis of collagen and proteoglycan. In one method, the bioartificial nucleus pulposus is subjected to cyclic loading of 0 to 5 MPa at frequencies of 0 to 20 Hz using a modified mechanical testing system (MTS). The nucleus pulposus cells can also be subjected to a load before they are mixed with the carrier material and injected into the support structure. In one method, NP cells cultured in dishes are placed in a hydraulic chamber filled with cell media. The chamber-cell assembly is then placed on a modified MTS where a piston applies a compressive cyclic load to the cells through the fluid media.

The bioartificial nucleus pulposus can then be used to replace a natural nucleus pulposus that has degenerated in an intervertebral disc. This involves removing the natural nucleus pulposus from the intervertebral disc and introducing the bioartificial nucleus pulposus in its place. Any suitable method can be used for replacing the natural nucleus pulposus with the bioartificial nucleus pulposus. In a typical method, the annulus fibrosus of the disc is cut laterally to remove a small section and thereby form a hole that allows removal of the natural NP and insertion of the bioartificial NP.

The bioartificial nucleus pulposus may potentially replace spinal fusion as the standard treatment method for degenerative disc disease. The bioartificial NP will allow surgeons to replace only the NP with a device that does not have to be fixed to the surrounding vertebrae. The vertebrae will not have to be immobilized; therefore, the patient will retain a full range of motion in addition to relieving pain.

Alternatively, the bioartificial nucleus pulposus can be used to produce a bioartificial intervertebral disc adapted for replacing a natural intervertebral disc which has degenerated in the spine of a patient. The entire degenerated disc can be replaced instead of just the nucleus pulposus. The bioartificial intervertebral disc comprises a hollow disc adapted for use as part of an intervertebral disc, and the bioartificial nucleus pulposus contained within the hollow disc. The hollow disc comprises an annulus and first and second endplates attached to opposing faces of the annulus. In a preferred embodiment, the hollow disc is a natural intervertebral disc with its natural nucleus pulposus removed. The natural intervertebral disc has an annulus comprising collagen fibers and first and second endplates comprising cartilage. However, the hollow disc could also be made of any other materials suitable for functioning as part of an intervertebral disc in a body, such as plastics or other polymers. Typically, the annulus will be made from a tough fibrous material. The method of replacing the natural intervertebral disc involves providing the hollow disc and introducing the bioartificial nucleus pulposus into the hollow disc to form the bioartificial intervertebral disc. The bioartificial NP can be introduced by any suitable means, such as by cutting a small hole in the annulus of the disc. The natural intervertebral disc is removed from between a pair of vertebrae in the patient's spine. Then, the bioartificial intervertebral disc is introduced between the pair of vertebrae. The bioartificial NP could also be introduced into the hollow disc after introducing the hollow disc between the vertebrae.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. A method of producing a bioartificial nucleus pulposus adapted for replacing at least a portion of a natural nucleus pulposus in an intervertebral disc in a spinal column of a human or animal patient, the method comprising:
   forming an artificial support structure from a biodegradable material, the support structure having a plurality of pores;
   suspending a plurality of nucleus pulposus cells within a carrier material;
   introducing the carrier material and cells into the pores of the support structure to produce the bioartificial nucleus pulposus; and
   applying a cyclic load in vitro to the nucleus pulposus cells;
   the biodegradable material of the support structure degrading in the body of the patient to leave a gel-like nucleus pulposus material established by the nucleus pulposus cells.

2. A method according to claim 1 comprising the additional step of culturing the bioartificial nucleus pulposus in vitro for at least about 1 week.

3. A method according to claim 1 wherein the support structure is formed by casting a biodegradable polymer in a mold containing a plurality of dissolvable objects, and wherein the casting is conducted multiple times to strengthen the support structure.

4. A method according to claim 1 wherein the nucleus pulposus cells are subjected to cyclic loading of 0 to 5 MPa at frequencies of 0 to 20 Hz.

5. A method of replacing at least a portion of a natural nucleus pulposus with a bioartificial nucleus pulposus in an intervertebral disc in a spinal column of a human or animal patient, the method comprising:

forming an artificial support structure from a biodegradable material, the support structure having a plurality of pores;

suspending a plurality of nucleus pulposus cells within a carrier material;

introducing the carrier material and cells into the pores of the support structure to produce the bioartificial nucleus pulposus;

applying a cyclic load in vitro to the nucleus pulposus cells;

removing at least a portion of the natural nucleus pulposus from the intervertebral disc; and introducing the bioartificial nucleus pulposus into the intervertebral disc in place of the removed natural nucleus pulposus;

the biodegradable material of the support structure degrading in the body of the patient to leave a gel-like nucleus pulposus material established by the nucleus pulposus cells.

6. A method according to claim 5 wherein the nucleus pulposus cells are subjected to cyclic loading of 0 to 5 MPa at frequencies of 0 to 20 Hz.

\* \* \* \* \*